United States Patent [19]
Ganz et al.

[11] Patent Number: 5,624,379
[45] Date of Patent: Apr. 29, 1997

[54] ENDOSCOPIC PROBE WITH DISCRETE ROTATABLE TIP

[75] Inventors: Robert A. Ganz; Jonathan Kagan; Brian D. Zelickson, all of Minneapolis; Ricci D. Smelser, Maple Lake, all of Minn.

[73] Assignee: G. I. Medical Technologies, Inc., Minneapolis, Minn.

[21] Appl. No.: 543,180

[22] Filed: Oct. 13, 1995

[51] Int. Cl.$^6$ ..................................................... A61B 1/00
[52] U.S. Cl. ........................... 600/104; 128/751; 128/772
[58] Field of Search ........................ 600/104, 106, 600/107; 606/205, 167, 170, 174; 128/751, 772

[56] References Cited

U.S. PATENT DOCUMENTS

| | | |
|---|---|---|
| 2,708,437 | 5/1955 | Hutchins . |
| 3,552,384 | 1/1971 | Pierie . |
| 3,631,848 | 1/1972 | Muller . |
| 3,777,743 | 12/1973 | Binard et al. . |
| 3,834,021 | 9/1974 | White et al. . |
| 4,245,624 | 1/1981 | Komiya ................................. 600/106 |
| 4,456,017 | 6/1984 | Miles . |
| 4,573,470 | 3/1986 | Samson et al. . |
| 4,619,263 | 10/1986 | Frisbie et al. . |
| 4,633,880 | 1/1987 | Osypka et al. . |
| 4,641,654 | 2/1987 | Samson et al. . |
| 4,664,113 | 5/1987 | Frisbie et al. . |
| 4,832,048 | 5/1989 | Cohen . |
| 4,920,980 | 5/1990 | Jackowski . |
| 4,945,920 | 8/1990 | Clossick . |
| 4,960,134 | 10/1990 | Webster, Jr. . |
| 5,018,530 | 5/1991 | Rank et al. . |
| 5,100,430 | 3/1992 | Avellanet et al. ................... 128/751 X |
| 5,125,896 | 6/1992 | Hojeibane . |
| 5,156,633 | 10/1992 | Smith . |
| 5,254,130 | 10/1993 | Poncet et al. ........................ 606/205 X |
| 5,273,051 | 12/1993 | Wilk . |
| 5,318,528 | 6/1994 | Heaven et al. ........................ 606/205 X |
| 5,365,942 | 11/1994 | Shank .................................... 128/772 |
| 5,386,818 | 2/1995 | Schneebaum et al. .................. 600/104 |
| 5,391,174 | 2/1995 | Weston . |
| 5,392,789 | 2/1995 | Slater et al. . |
| 5,417,203 | 5/1995 | Tovey et al. ......................... 606/205 X |

FOREIGN PATENT DOCUMENTS 257747  3/1965  Australia .

*Primary Examiner*—Beverly M. Flanagan
*Attorney, Agent, or Firm*—Merchant, Gould, Smith, Edell, Welter & Schmidt, P.A.

[57] ABSTRACT

An endoscopic probe has an elongate flexible member and a radially extending tip rotatably mounted on a remote end thereof. A wire extends through the elongate flexible member and into the tip. The wire rotates relative to the elongate flexible member to rotate the radially extending tip to any desired orientation about the axis of the elongate flexible member.

34 Claims, 2 Drawing Sheets

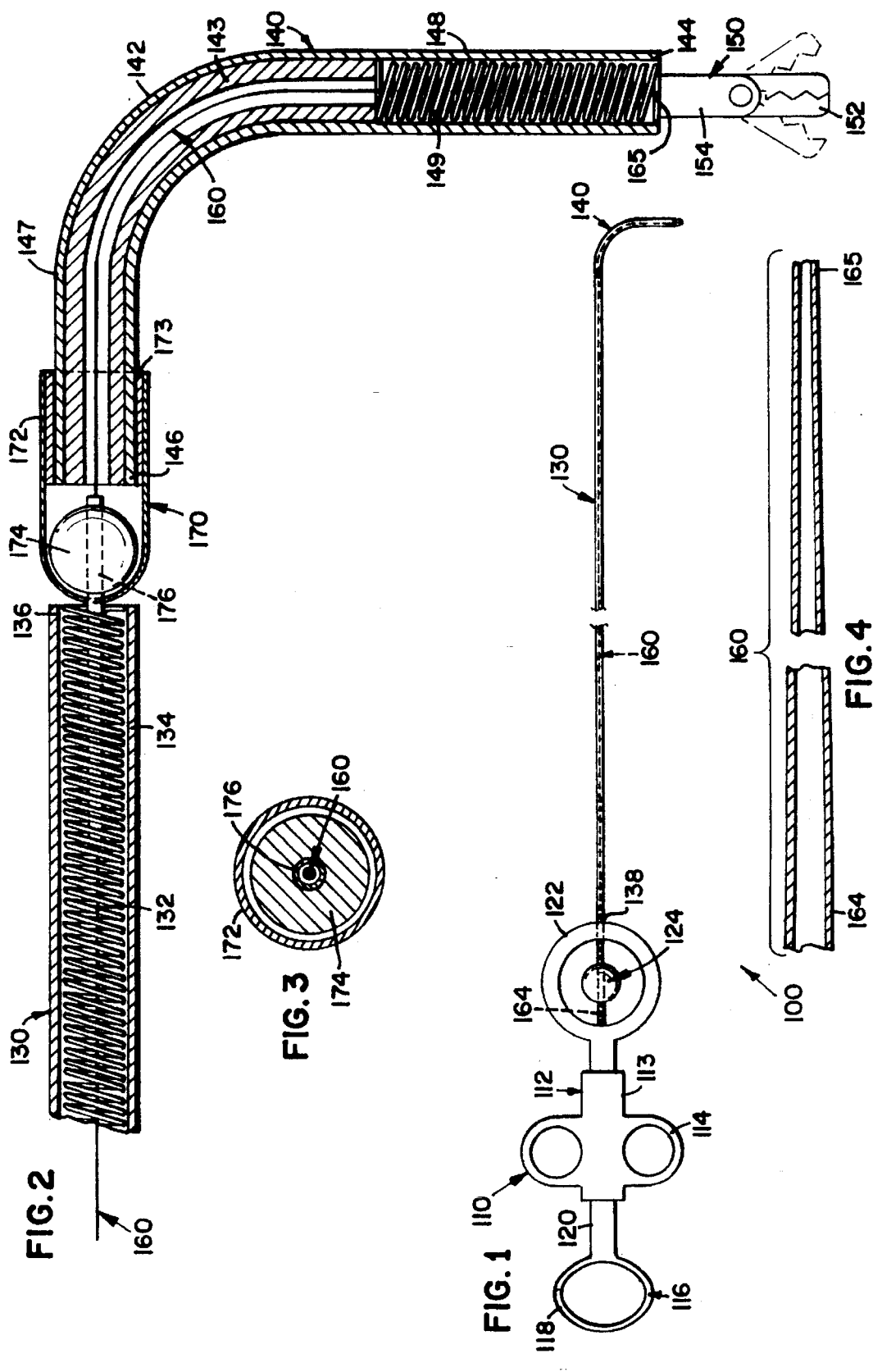

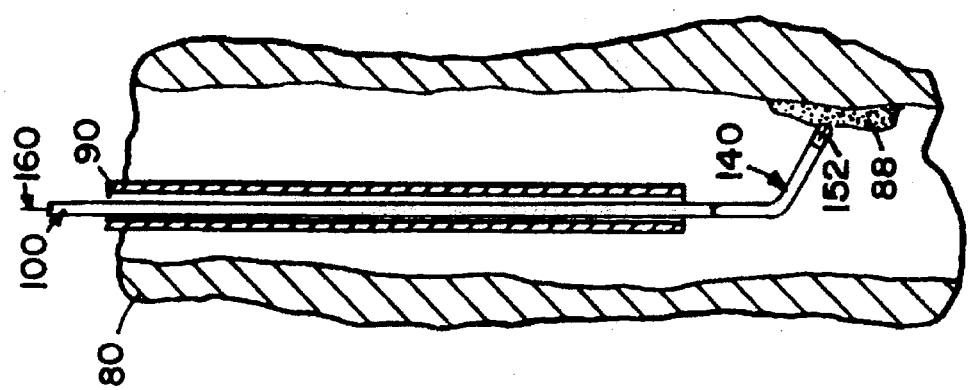
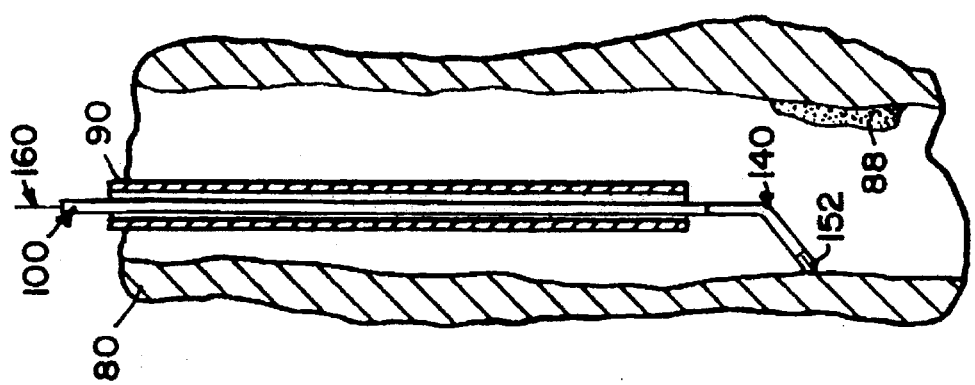
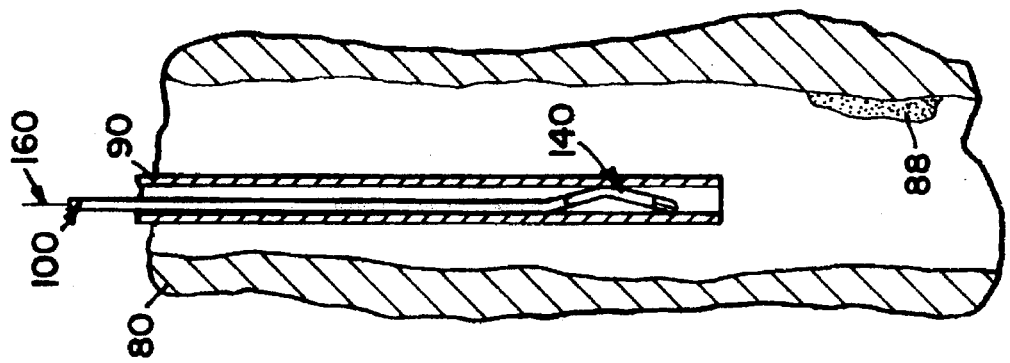

ENDOSCOPIC PROBE WITH DISCRETE ROTATABLE TIP

FIELD OF THE INVENTION

The present invention relates to medical devices and more particularly, to an endoscopic probe having a remote tip which is rotatable and biased to extend radially from the axis of rotation.

BACKGROUND OF THE INVENTION

Numerous medical procedures require access to an internal portion of a person's body (either directly or indirectly). Typically, the less intrusive the access, the better. As a result, many such procedures are performed with one or more tools at the remote end of an elongate flexible member which are inserted into the patient's body and operated remotely. For example, in order to obtain a sample of esophagus tissue, a practitioner inserts an endoscope into the patient's esophagus and then feeds a cable (made of coiled stainless steel wire) through the endoscope and into proximity with the patient's esophagus. Biopsy jaws are connected to the remote end of the cable and are operable to capture a tissue sample. The jaws are actuated by axial movement of a wire nested within the cable.

As can be appreciated by anyone who has attempted to unlock a car door with a coat hanger, it is one thing to get the coat hanger into proximity with the door latch, and it is quite another to hook the latch and pull it open. The same can be said for operation of an endoscopic probe of the type described above, particularly when one recognizes that the probe must be inserted through a tube and yet perform a task on a body part that is typically radially displaced from the axis of the tube. In other words, the endoscope gets the biopsy jaws down into the patient's esophagus, but the tissue may be off to the side. One approach to overcome this problem has been to deflect the endoscope to aim the biopsy jaws in the desired direction. However, the size of the endoscope and/or anatomical constraints place significant limitations on this practice.

U.S. Pat. No. 4,945,920 discloses a device having a radially extending tip which can be maneuvered relative to a patient by rotating the entire device within the endoscope. However, this device is difficult to operate because rotation of the entire device can cause "twist" to accumulate, and friction between the device and the endoscope makes it difficult to effect incremental movements of the remote tip. In other words, the torque tends to build along the device until resistance due to static friction is overcome, at which point the relative smaller resistance due to kinetic friction allows the torque to be released essentially all at once, thereby causing whipping of the distal portion of the device. Thus, a need remains for an endoscopic probe that is easy to operate and effective in use.

SUMMARY OF THE INVENTION

A preferred embodiment of the present invention provides an endoscopic probe having a tip that rotates about the longitudinal axis of the probe and extends radially therefrom. An elongate flexible member extends from a handle to a remote end which is connected to the tip by means of a swivel. A wire extends through the flexible member and the swivel and into the radially extending tip. A rotating portion of the handle is rotated relative to a base portion of the handle to rotate the tip relative to the flexible member. A tool, such as biopsy jaws, may be selectively connected to the remote end of the wire, proximate the distal end of the tip, such that the tool may be operated by axial movement of the wire relative to the flexible member.

One advantage of the present invention is that the radially extending tip is able to readily access tissue not directly aligned with the endoscope. Also, the biopsy jaws occupy a more straightforward or head-on bite angle relative to the target tissue. In the preferred embodiment, the tip is generally L-shaped and made of a resilient material capable of deforming to accommodate insertion into an endoscope and capable of reassuming its L-shaped configuration upon exiting same.

Another advantage of the present invention is that the rotatable tip allows a sample to be taken in any direction from the longitudinal axis of the endoscope. Also, the swivel allows rotation of the relatively short tip relative to the relatively long flexible member, thereby minimizing the accumulation of torque which can lead to whipping of the remote end. Moreover, the means for actuating both the rotation of the tip and the opening and closing of the biopsy jaws are conveniently incorporated into the handle.

The combination of the radially extending tip and the internal torque transmitting member make the present invention easier to use and more effective in use. These advantages and others will become apparent to those skilled in the art upon a more detailed description of the preferred embodiment.

BRIEF DESCRIPTION OF THE FIGURES OF THE DRAWING

With reference to the Figures of the Drawing, wherein like numerals represent like parts and assemblies throughout the several views:

FIG. 1 is a plan view of a preferred embodiment probe constructed according to the principles of the present invention;

FIG. 2 is a sectioned plan view of a remote end of the preferred embodiment probe of FIG. 1;

FIG. 3 is a sectioned end view of the remote end of FIG. 2;

FIG. 4 is a sectioned fragmentary view of a wire extending through the preferred embodiment probe of FIG. 1;

FIG. 5 is a plan view of the remote end of FIG. 2, shown in a first position relative to an endoscope inserted into a patient's esophagus;

FIG. 6 is a plan view of the remote end of FIG. 2, shown in a second position relative to an endoscope inserted into a patient's esophagus; and FIG. 7 is a plan view of the remote end of FIG. 2, shown in a third position relative to an endoscope inserted into a patient's esophagus.

DETAILED DESCRIPTION OF THE PREFERRED EMBODIMENT

A preferred embodiment endoscopic probe constructed according to the principles of the present invention is designated as 100 in FIGS. 1–7. The preferred embodiment probe 100 is designed specifically for taking a biopsy sample from a person's esophagus. However, those skilled in the art will recognize that the present invention is not limited to this particular application. For example, similar probes could be used in any of various procedures in which an endoscope or other relatively stiff tube provides access to an internal portion of a patient's body, including cardiac, gastrointestinal, urological, pulmonary, orthopedic, general surgery, ENT, laparoscopy, and/or radiology procedures.

As shown in FIG. 1, the probe 100 includes a handle 110 having a plunger or sliding portion 112, a base portion 116, and a rotating portion 124, each of which is made of plastic. The sliding portion 112 includes a central body 113 and a pair of closed loops 114 extending from opposite sides thereof. Each of the loops 114 is sized and configured to receive a person's finger. The base portion 116 includes a shaft 120 disposed within and slidable relative to the body 113 of the sliding portion 112. Connected to one end of the shaft 120 is a closed loop 118 which is sized and configured to receive a person's thumb. Connected to an opposite end of the shaft 120 is another closed loop 122.

The rotating portion 124 of the handle 110 is a ball which is operatively connected to a wire 160 and disposed within the confines of the closed loop 122. In the preferred embodiment 100, the ball 124 is fixed to the wire 160, thereby preventing axial and/or rotational movement of one relative to the other. The size of the loop 122 is sufficiently large to accommodate axial movement of the ball 124. However, those skilled in the art will recognize that the ball 124 could be keyed to the wire 160 a manner that allowed relative axial movement between the ball 124 and the wire 160 but not relative rotational movement between the ball 124 and the wire 160.

As shown in FIGS. 1–2, the probe 100 further includes an elongate flexible member 130 which extends from a first end 138, proximate the handle 110, to a second, remote end 136. The first end 138 is anchored to the sliding portion 112 of the handle 110. In the preferred embodiment 100, the elongate flexible member 130 is at least one meter long and includes a coil of stainless steel wire 132 disposed within a polyurethane tube 134. Those skilled in the art will recognize that the plastic tube 134 is optional and that both it and/or the elongate flexible member 130 could be made from other suitable materials. Moreover, the length of the elongate flexible member 130 may vary according to its intended application.

The probe 100 further includes a curved tip 140 which extends from a first end 146, proximate the remote end 136 of the elongate flexible member 130, to a second, distal end 144. In the preferred embodiment 100, the curved tip 140 is less than ten centimeters in length and includes a teflon tube 143 disposed within a polyurethane tube 142. Those skilled in the art will recognize that the tip 140 could be made from other suitable materials. The curved tip 140 is preformed to assume a shape substantially as shown in FIG. 2, wherein a first segment 147 is a generally co-linear extension of the elongate flexible member 130, and a second segment 148 extends generally transverse to the first segment 147. Although the preferred embodiment segments 147 and 148 extend perpendicular to one another, those skilled in the art will recognize that this preformed angle, as well as the overall length of the tip 140, may vary according to the application for which it is intended. Also, a stainless steel coil 149 may be disposed within the second segment 148 to enhance structural integrity. The stainless steel coil 149 occupies a portion of the plastic tube 142 exclusive of the teflon tube 143. The curved tip 140 is sufficiently resilient to accommodate substantial straightening thereof and then to subsequently return to its preformed, generally L-shaped configuration.

A tool 150 is supported by the curved tip 140 proximate its distal end 144. In the preferred embodiment 100, the tool 150 includes a pair of biopsy jaws 152 and a capsule 154.

The jaws 152 are pivotally connected to one another and open and close to collect a tissue sample. Those skilled in the art will recognize that numerous other tools could be substituted for the biopsy jaws 152 and the capsule 154 shown in FIG. 2. For example, the probe 100 could be fitted with any of various retrieval devices, sewing devices, needles, snares, knives, scissors, etc.

The wire 160 extends from a first end 164, proximate the handle 110, to a second, remote end 165. The first end or terminal portion 164 of the wire 160 spans the closed loop 122 on the handle 110 and is anchored to the ball 124. The first end 164 of the wire 160 includes enlargements or stops disposed within cavities in the sliding portion 112. The stops and the cavities cooperate to transmit axial motion of the sliding portion 112 to the wire 160 but do not impede rotation of the wire 160 relative to the sliding portion 116. Those skilled in the art will recognize that this interconnection may be accomplished in other manners, as well. For example, a ball and socket joint would similarly allow free rotation of the wire relative to the sliding portion while transmitting axial force therebetween. In either case, the wire 160 and the sliding portion 112 may be said to be operatively connected in a manner that allows relative rotation and facilitates axial transmission.

The ball 124 and the wire 160 are rotatable about the axis of the wire 160 relative to the sliding portion 112 of the handle 110, the base portion 116 of the handle 110, and the elongate flexible member 130. The wire 160 extends through the elongate flexible member 130 and into the second segment 148 of the curved tip 140. The remote end 165 of the wire 160 is connected to the biopsy jaws 152, and axial movement of the wire 160 (relative to the base portion 116 of the handle 110 and the elongate flexible member 130) operates the jaws 152 in a manner already known in the art.

In the preferred embodiment 100, the wire 160 is made of stainless steel. As shown in FIG. 4, the wire 160 is hollow or tubular and has a diameter that decreases from the first or handle end 164 to the second or remote end 165. The decreasing diameter may be accomplished by a constant taper or discrete decrements along the length thereof. In either case, the decreasing diameter facilitates smoother torque transmission and more effective operation of the apparatus 100. The hollow configuration provides a means for placing the remote end 165 in fluid communication with the handle end 164. Those skilled in the art will recognize that both the tapering of the wire 160 and its hollow configuration are optional, and that alternative torque transmitting members, such as a solid wire, a composite wire, or a braided cable, could be substituted for the wire 160.

In the preferred embodiment 100, the curved tip 140 is rotatably mounted to the elongate flexible member 130 by means of a swivel or ball and socket joint 170. In particular, a stainless steel tube 176 is welded to the elongate flexible member 130 and extends beyond the remote end 136 thereof. The tube 176 extends into a sleeve 172 and then through a stainless steel ball 174, to which the tube 176 is welded. The sleeve 172 curves around the ball 174 on the side proximate the elongate flexible member 130 and thereby provides the socket portion of the joint 170. The sleeve 172 extends away from the elongate flexible member 130 and is secured to the curved tip 140 by means of cyanoacyrilate adhesive 173. Those skilled in the art will recognize that these components could be manufactured from other materials and/or secured to one another by different methods, including soldering, for example.

As shown in FIG. 3, the wire 160 extends through the tube 176 and into the curved tip 140. Torque applied to the rotating portion 124 of the handle 110 causes the wire 160, the sleeve 172, and the curved tip 140 to rotate relative to the elongate flexible member 130, the tube 176, and the ball 174. With a tip 140 that is both curved and freely rotatable, the probe 100 is easy to use and suitable for a variety of endoscopic procedures. Also, the tip 140 may be provided in different sizes and/or configurations according to the parameters for different procedures. Those skilled in the art will also recognize that any given tip will tend to direct the biopsy jaws or other tool at a substantially constant angle regardless of the orientation of the tip relative to the flexible member.

The effective angle of the tip 140 (or any curved tip) may be controlled simply by varying the amount of the tip that projects beyond the end of the endoscope. In order to minimize frictional resistance and possible whipping, the tip 140 should first be pushed entirely out of the endoscope and rotated to face in the desired direction. The tip 140 may then be drawn back into endoscope to arrive at a desired angle of radial deflection.

Operation of the probe 100 is described with reference to an esophageal biopsy procedure, several steps of which are illustrated in FIGS. 5–7. An endoscope 90, which may be described as a relatively stiff tube or device defining a lumen, is inserted down the esophagus 80 of a patient, and then the probe 100 is fed through the endoscope 90. The length of the second segment 148 is greater than the diameter of the relatively stiff tube 90. As shown in FIG. 5, the tip 140 is temporarily straightened to facilitate passage through the endoscope 90. As shown in FIG. 6, the tip 140 returns to its preformed configuration upon exiting the remote end of the endoscope 90. The curvature of the tip 140 places the biopsy jaws 152 at a desirable angle relative to the sidewalls of the persons esophagus 80 and also provides immediate access to radially displaced portions thereof. As shown in FIG. 7, the tip 140 is then rotated about the axis of the flexible member 130 (by rotating the ball 124 on the handle 110) to arrive at the desired tissue location 88. Next, the jaws 152 are opened and closed (by sliding the plunger 112 on the handle 110 back and forth) to collect the tissue sample. Finally, the probe 100 is withdrawn from the endoscope 90, which in turn, is withdrawn from the patient's esophagus 80.

Although the present invention has been described with reference to a preferred embodiment and a particular application, the foregoing disclosure will enable those skilled in the art to realize additional applications and embodiments. Thus, the scope of the present invention is to be limited only to the extent of the following claims.

The invention claimed is:

1. A medical probe of a type inserted through an endoscope having a longitudinal axis, comprising:
   an elongate flexible member having a user accessible end and a remote end;
   a second member rotatably mounted to said remote end and sized and configured for insertion into the endoscope; and
   a rotating means, operatively connected to said second member, for rotating said second member, exclusive of said elongate flexible member, about the longitudinal axis of the endoscope.

2. A medical probe according to claim 1, wherein said second member is made of a resilient material and preformed to assume a curved configuration when unstressed.

3. A medical probe according to claim 1, wherein a torque transmitting member is disposed within said elongate flexible member, and said torque transmitting member has a user accessible end and a remote end, and said remote end of said torque transmitting member is connected to said second member in such a manner that rotation of said user accessible end of said torque transmitting member causes rotation of said second member.

4. A medical probe according to claim 3, wherein said torque transmitting member is a stainless steel wire.

5. A medical probe according to claim 3, wherein said torque transmitting member is a hollow wire.

6. A medical probe according to claim 3, wherein a ball and socket are interconnected between said second member and said remote end of said elongate flexible member.

7. A medical probe according to claim 3, wherein said torque transmitting member is axially movable relative to said elongate flexible member.

8. A medical probe according to claim 7, further comprising a tool connected to said remote end of said torque transmitting member and operable in response to axial movement of said torque transmitting member relative to said elongate flexible member.

9. A medical probe according to claim 3, wherein said torque transmitting member has a relatively larger diameter proximate said user accessible end thereof, and said torque transmitting member has a relatively smaller diameter proximate said remote end thereof.

10. A medical probe according to claim 1, wherein a ball and socket are interconnected between said second member and said remote end of said elongate flexible member.

11. A medical probe according to claim 1, wherein said second member is resilient, and said second member deforms toward a relatively more straight configuration during passage through the endoscope, and said second member returns to a relatively more curved configuration upon exiting the endoscope.

12. A medical probe according to claim 11, wherein when said second member returns to said relatively more curved configuration upon exiting the endoscope, a distal section of said second member extends substantially perpendicular to said elongate flexible member proximate said remote end thereof.

13. A medical probe according to claim 1, further comprising a tool supported by a distal end of said second member.

14. A medical probe according to claim 13, wherein said tool is oriented at an angle relative to a remote portion of said elongate flexible member, and said angle tends to remain substantially constant during rotation of said second member.

15. A medical probe according to claim 1, wherein said elongate flexible member includes a stainless steel coil.

16. A medical probe according to claim 15, wherein said stainless coil is nested within a plastic tube.

17. A medical probe according to claim 1, wherein said second member includes a teflon tube nested within a plastic tube.

18. A medical probe according to claim 17, wherein said second member further includes a stainless steel coil nested within a portion of said plastic tube exclusive of said teflon tube.

19. A medical probe according to claim 1, further comprising a handle connected to said user accessible end of said elongate flexible member.

20. A medical probe according to claim 19, further comprising biopsy jaws operatively connected to said handle in such a manner that relative movement between a first handle member and a second handle member causes movement of said biopsy jaws relative to one another.

21. A medical probe according to claim 20, wherein relative movement between a third handle member and said second handle member causes rotation of said second member.

22. A medical probe according to claim 1, wherein a ball is secured to said remote end of said elongate flexible member, and a wire extends through at least a portion of said elongate flexible member, and through said ball, and through at least a portion of said second member.

23. A medical probe according to claim 22, wherein a sleeve has a first end which forms a socket about said ball, and said sleeve has a second, opposite end which is secured to said second member, and said wire, said sleeve, and said second member rotate as a unit relative to said ball and said elongate flexible member.

24. A medical probe according to claim 23, wherein a tube extends through said ball and a portion of said elongate flexible member, and said wire extends through said tube.

25. An endoscopic probe, comprising:
- a handle;
- a first elongate flexible member having a first end operatively connected to said handle, and having a second, remote end;
- a tool;
- a ball and socket joint interconnected between said tool and said remote end of said first elongate flexible member; and
- a second elongate flexible member having a first end operatively connected to said handle, and having a second, remote end operatively connected to said tool, wherein said second elongate flexible member extends through said first elongate flexible member and said ball and socket joint, and rotation of said second elongate flexible member causes rotation of said tool exclusive of said first elongate flexible member.

26. An endoscopic probe according to claim 25, wherein a curved resilient member is interconnected between said ball and socket joint and said tool, and said second elongate flexible member extends through said curved resilient member.

27. An endoscopic probe according to claim 25, wherein said handle includes a base portion and a rotating portion, and said second elongate flexible member is operatively connected to said rotating portion, and rotation of said rotating portion relative to said base portion causes rotation of said second elongate flexible member and said tool relative to said first elongate flexible member.

28. An endoscopic probe according to claim 27, wherein said handle further includes a sliding portion, and said second elongate flexible member is secured operatively connected to said sliding portion, and sliding of said sliding portion relative to said base portion actuates said tool.

29. An endoscopic probe according to claim 25, wherein said tool includes a pair of biopsy jaws pivotally mounted relative to one another.

30. An apparatus suitable for performing a task relative to an internal portion of a person's body, comprising:
- a relatively stiff device defining a tubular lumen, wherein the device is sized and configured for at least partial insertion into the person's body;
- a relatively flexible hollow member sized and configured for insertion through said relatively stiff device and toward the internal portion of the person's body;
- a tip mounted on a remote end of said relatively flexible hollow member, wherein the tip includes a first segment, a second segment, and a biasing means interconnected therebetween, and said first segment is a substantially co-linear extension of said relatively flexible hollow member, and said biasing means biases said second segment toward an angle relative to said first segment, and the length of said second segment is greater than the diameter of said relatively stiff device, and said second segment deflects relative to said first segment and against said biasing means to facilitate insertion through said relatively stiff device; and
- a wire extending through said relatively flexible hollow member and into said tip, wherein rotation of said wire relative to said relatively flexible hollow member causes rotation of said tip relative to said relatively flexible hollow member.

31. An apparatus according to claim 30, wherein said first segment and said second segment are portions of a continuous piece of resilient material which functions as said biasing means.

32. An apparatus according to claim 30, wherein said wire is hollow.

33. An apparatus according to claim 30, wherein said wire is relatively thicker proximate a user accessible end thereof, and said wire is relatively thinner proximate said tip.

34. An apparatus according to claim 30, wherein a swivel is interconnected between said tip and said relatively flexible hollow member.

\* \* \* \* \*